(12) United States Patent
Wigerinck et al.

(10) Patent No.: US 6,649,651 B1
(45) Date of Patent: Nov. 18, 2003

(54) HEXAHYDROFURO[2,3-B]FURAN-3-YL-N{3 [(1,3-BENZODIOXOL-5-YLSULFONYL) (ISOBUTYL)AMINO]-1-BENZYL-2-HYDROXYPROPYL}CARBAMATE AS RETROVIRAL PROTEASE INHIBITOR

(75) Inventors: Piet T. B. P. Wigerinck, Vosselaar (BE); Guangyang Wang, Gaihersburg, MD (US); Michael Eissenstat, Frederick, MD (US); John W. Erickson, Frederick, MD (US)

(73) Assignee: Tibotec Pharmaceuticals LTD (IE)

( * ) Notice: Subject to any disclaimer, the term of this patent is extended or adjusted under 35 U.S.C. 154(b) by 0 days.

(21) Appl. No.: 10/089,991

(22) PCT Filed: Oct. 6, 2000

(86) PCT No.: PCT/EP00/09917

§ 371 (c)(1),
(2), (4) Date: Dec. 23, 2002

(87) PCT Pub. No.: WO01/25240

PCT Pub. Date: Apr. 12, 2001

Related U.S. Application Data (60) Provisional application No. 60/157,850, filed on Oct. 6, 1999.

(51) Int. Cl.⁷ .............................................. A61K 31/36
(52) U.S. Cl. ........................................ 514/464; 549/435
(58) Field of Search .......................... 549/435; 514/464, 514/465

(56) References Cited

FOREIGN PATENT DOCUMENTS

| WO | WO 94/05639 | 3/1994 |
|----|-------------|--------|
| WO | WO 95/06030 | 3/1995 |
| WO | WO 96/33184 | 10/1996 |
| WO | WO 99/67254 | 12/1999 |
| WO | WO 99/67417 | 12/1999 |

OTHER PUBLICATIONS

Ghosh et al., "Potent HIV Protease Inhibitors Incorporating High–Affinity P2–Ligands and (R)–(hydroxyethyl)amino-sulfonamide isostere," Bioorg. Med. Chem. Lett., vol. 8, No. 6 pp. 687–690 (1998).

*Primary Examiner*—Amelia Owens (57) ABSTRACT

Novel bis-tetrahydrofuran benzodioxolyl sulfonamide compounds which are surprisingly effective protease inhibitors. The invention also relates to pharmaceutical compositions, methods of inhibiting retrovirus proteases, in particular multidrug resistant retrovirus proteases, methods of treating or combating infection or disease associated with retrovirus infection in a mammal, and methods of inhibiting viral replication.

17 Claims, 2 Drawing Sheets

HEXAHYDROFURO[2,3-B]FURAN-3-YL-N{3[(1,3-BENZODIOXOL-5-YLSULFONYL)(ISOBUTYL)AMINO]-1-BENZYL-2-HYDROXYPROPYL}CARBAMATE AS RETROVIRAL PROTEASE INHIBITOR

This application is a national stage filing under 35 U.S.C. § 371 of international application no. PCT/EP00/09917, filed on Oct. 6, 2000, which claims priority to U.S. Pat. application Ser. No. 60/157,850, filed on Oct. 6, 1999.

This application claims priority benefit to U.S. Provisional Application No. 60/157,850, filed on Oct. 6, 1999, the contents of which are expressly incorporated by reference herein.

The present invention relates to novel bis-tetrahydrofuran benzodioxolyl sulfonamide compounds, compositions comprising them and processes for their preparation. It also relates to the use of the present compounds as pharmaceutical active compounds for the therapy and prophylaxis of retroviral infections, particularly HIV infections, and most particularly for multidrug resistant HIV infections in a mammal.

Resistance of HIV against inhibitors is a major cause of therapy failure. Half of the patients receiving anti-HIV combination therapy do not respond fully to the treatment, mainly because of resistance of the virus to one or more drugs used. Moreover, it has been shown that resistant virus is carried over to newly infected individuals, resulting in severely limited therapy options for these drug-naive patients. Therefore, there is a need in the art for new compounds for retrovirus therapy, more particularly for AIDS therapy. The need in the art is particularly acute for compounds that are active not only on wild type virus, but also on the increasingly more common resistant viruses. Moreover, protease inhibitors are commonly administered to AIDS patients in combination with other anti-HIV compounds such as, for instance NRTIs and/or NNRTIs. This causes a high pill burden upon the patient. One way of reducing this pill burden is finding anti-HIV compounds like protease inhibitors with good bioavailability, i.e. a favorable pharmacokinetic and metabolic profile, such that the daily dose can be minimized. Another important characteristic of a good protease inhibitor, and for anti-HIV compounds in general, is that protein plasma binding of the protease inhibitor has minimal or even no effect on its potency.

Several published patent applications disclose HIV protease inhibitors. For instance, WO 95/06030 discloses HIV protease inhibitors with a hydroxyethylamino sulfonamide core structure. Also Ghosh et al. (Bioorganic & Medicinal Chemistry Letters, 8, 1998, 687–690) discloses hydroxyethylamino sulfonamide HIV protease inhibitors.

The compounds of the present invention are surprisingly effective HIV protease inhibitors in terms of their activity over a broad range of HIV mutants and in terms of their bioavailability. Additional objects and advantages will be set forth in part in the description which follows, and in part will be obvious from the description, or may be learned by practice of the invention. The objects and advantages of the invention will be realized and attained by means of the elements and combinations particularly pointed out in the claims.

DETAILED DESCRIPTION OF THE INVENTION

In order that the invention herein described may be more fully understood, the following detailed description is set forth.

The present invention relates to the compounds having the formula (I)

and N-oxides, salts, esters, stereoisomeric forms, racemic mixtures, prodrugs and metabolites thereof. The molecular structure depicted above is named hexahydrofuro[2,3-b]furan-3-yl-N-{3-[(1,3-benzodioxol-5-ylsufonyl)(isobutyl)amino]-1-benzyl-2-hydroxypropyl} carbamate.

This invention also envisions the quaternization of the nitrogen atoms of the present compounds. A basic nitrogen can be quaternized with any agent known to those of ordinary skill in the art including, for instance, lower alkyl halides, dialkyl sulfates, long chain halides and aralkyl halides. Water or oil-soluble or dispensible products may be obtained by such quaternization.

The term prodrug as used throughout this text means the pharmacologically acceptable derivatives such as esters, amides and phosphates, such that the resulting biotransformation product of the derivative is the active drug as defined in the compounds of formula (I). The reference by Goodman and Gilman (The Pharmacological Basis of Therapeutics, 8$^{th}$ ed, McGraw-Hill, Int. Ed. 1992. "Biotransformation of Drugs", p 13–15) describing prodrugs generally is hereby incorporated. Typical examples of prodrugs are described for instance in WO 99/33795, WO 99/33815, WO 99/33793 and WO 99/33792 all incorporated herein by reference.

Prodrugs are characterized by excellent aqueous solubility, increased bioavailability and are readily metabolized into the active inhibitors in vivo.

For therapeutic use, the salts of the compounds of formula (I) are those wherein the counterion is pharmaceutically or physiologically acceptable. However, salts having a not-pharnaceutically acceptable counterion may also find use, for example, in the preparation or purification of a pharmaceutically acceptable compound of formula (I). All salts, whether pharmaceutically acceptable or not are included within the ambit of the present invention.

The pharmaceutically acceptable or physiologically tolerable addition salt forms which the compounds of the present invention are able to form can conveniently be prepared using the appropriate acids, such as, for example, inorganic acids such as hydrohalic acids, e.g. hydrochloric or hydrobrornic acid; sulfuric; nitric; phosphoric and the like acids; or organic acids such as, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The term salts also comprises the hydrates and the solvent addition forms which the compounds of the present invention are able to form. Examples of such forms are e.g. hydrates, alcoholates and the like.

The N-oxide forms of the present compounds are meant to comprise the compounds of formula (I) wherein one or several nitrogen atoms are oxidized to the so-called N-oxide.

The present compounds may also exist in their tautomeric forms. Such forms, although not explicitly indicated in the above formula are intended to be included within the scope of the present invention.

The term stereochemically isomeric forms of compounds of the present invention, as used hereinbefore, defines all possible compounds made up of the same atoms bonded by the same sequence of bonds but having different three-dimensional structures which are not interchangeable, which the compounds of the present invention may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of the present invention both in pure form or in admixture with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

It is clear to a person skilled in the art that the compounds of formula (I) contain 5 centers of chirality and thus exist as stereoisomeric forms. These 5 centers of chirality 5 are indicated with a numbered asterisk (*1, *2, *3, *4 and *5) in the figure below.

(I)

The absolute configuration of each asymmetric center may be indicated by the stereochemical descriptors R and S, this R and S notation corresponding to the rules described in Pure Appl. Chem. 1976. 45, 11–30. The preferred configuration of the bis-tetrahydrofuran ring is the one where carbon atom *1 has an R configuration, carbon atom *2 an S configuration and carbon atom *3 an R configuration, where carbon atom *1 has an S configuration, carbon atom *2 an R configuration and carbon atom *3 an S configuration. Carbon atom *4 is preferably in the S configuration and carbon atom *5 in the R configuration.

The following 32 enantiomeric forms in table 1 exist of the compound with basic structure (I). The chiral carbon atoms are named as shown in the figure above.

TABLE A

| Comp | *1 | *2 | *3 | *4 | *5 |
|---|---|---|---|---|---|
| a | R | R | R | R | R |
| b | R | R | R | R | S |
| c | R | R | R | S | R |
| d | R | R | S | R | R |
| e | R | S | R | R | R |
| f | S | R | R | R | R |
| g | R | R | R | S | S |
| h | R | R | S | R | S |
| i | R | S | R | R | S |
| j | S | R | R | R | S |
| k | R | R | S | S | R |
| l | R | S | R | S | R |
| m | S | R | R | S | R |
| n | R | S | S | R | R |
| o | S | R | S | R | R |
| p | S | S | R | R | R |
| q | R | R | S | S | S |
| r | R | S | R | S | S |
| s | S | R | R | S | S |
| t | R | S | S | R | S |
| u | S | R | S | R | S |
| v | R | S | S | S | R |
| w | S | R | S | S | R |
| x | S | S | S | R | R |
| y | S | S | R | S | R |
| z | S | S | R | R | S |
| aa | S | S | S | S | R |
| bb | S | S | S | R | S |
| cc | S | S | R | S | S |
| dd | S | R | S | S | S |
| ee | R | S | S | S | S |
| ff | S | S | S | S | S |

Compounds 1 and w are the preferred enantiomeric pure forms, in particular compound 1.

Compound 1, also referred to as Compound 14

Whenever used hereinafter, the term "compounds of formula (I)", or "the present compounds" or similar term is meant to include the compound as depicted above, their N-oxides, salts, esters, stereoisomeric forms, racemic mixtures, prodrugs and metabolites, as well as their quaternized nitrogen derivatives.

The present compounds can thus be used in animals, preferably in mammals, and in particular in humans as pharmaceuticals per se, in mixtures with one another or in the form of pharmaceutical preparations.

Furthermore, the present invention relates to pharmaceutical preparations which as active constituents contain an effective dose of at least one of the compounds of formula (I) and/or of a physiologically tolerable salt thereof in addition to customary pharmaceutically innocuous excipients and auxiliaries. The pharmaceutical preparations normally contain 0.1 to 90% by weight of a compound of formula (I) and/or its physiologically tolerable salts. The pharmaceutical preparations can be prepared in a manner known per se to one of skill in the art. For this purpose, at least one of a compound of formula (I) and/or its physiologically tolerable salts, together with one or more solid or liquid pharmaceutical excipients and/or auxiliaries and, if desired, in combination with other pharmaceutical active compounds, are brought into a suitable administration form or dosage form which can then be used as a pharmaceutical in human medicine or veterinary medicine.

Pharmaceuticals which contain a compound according to the invention and/or its physiologically tolerable salts can be administered orally, parenterally, e.g., intravenously, rectally, by inhalation, or topically, the preferred administration being dependent on the individual case, e.g., the particular course of the disorder to be treated. Oral administration is preferred.

The person skilled in the art is familiar on the basis of his expert knowledge with the auxiliaries which are suitable for the desired pharmaceutical formulation. Beside solvents, gel-forming agents, suppository bases, tablet auxiliaries and other active compound carriers, antioxidants, dispersants, emulsifiers, antifoams, flavor corrigents, preservatives, solubilizers, agents for achieving a depot effect, buffer substances or colorants are also useful.

Due to their antiretroviral properties, particularly their anti-HIV properties, especially their anti-HIV-1-activity, the compounds of the present invention are useful in the treatment of individuals infected by HIV and for the prophylaxis of these individuals. In general, the compounds of the present invention may be useful in the treatment of warm-blooded animals infected with viruses whose existence is mediated by, or depends upon, the protease enzyme. Conditions which may be prevented or treated with the compounds of the present invention, especially conditions associated with HIV and other pathogenic retroviruses, include AIDS, AIDS-related complex (ARC), progressive generalized lymphadenopathy (PGL), as well as chronic CNS diseases caused by retroviruses, such as, for example HIV mediated dementia and multiple sclerosis.

The compounds of the present invention or any subgroup thereof may therefore be used as medicines against above-mentioned conditions. Said use as a medicine or method of treatment comprises the systemic administration to HIV-infected subjects of an amount effective to combat the conditions associated with HIV and other pathogenic retroviruses, especially HIV-1. Consequently, the compounds of the present invention can be used in the manufacture of a medicament useful for treating conditions associated with HIV and other pathogenic retroviruses, in particular with medicaments with retroviral protease inhibitory action.

Also, the combination of an antiretroviral compound and a compound of the present invention can be used as a medicine. Thus, the present invention also relates to a product containing (a) a compound of the present invention, and (b) another antiretroviral compound, as a combined preparation for simultaneous, separate or sequential use in treatment of retroviral infections, in particular with multi-drug resistant retroviruses. Thus, to combat or treat HIV infections, or the infection and disease associated with HIV infections, such as Acquired Immunodeficiency Syndrome (AIDS) or AIDS Related Complex (ARC), the compounds of this invention may be co-administered in combination with for instance, binding inhibitors, such as, for example, dextran sulfate, suramine, polyanions, soluble CD4; fusion inhibitors, such as, for example, T20, T1249, SHC-C; co-receptor binding inhibitors, such as, for example, AMD 3100 (Bicyclams), TAK 779; RT inhibitors, such as, for example, foscarnet and prodrugs; nucleoside RTIs, such as, for example, AZT, 3TC, DDC, DDI, D4T, Abacavir, FTC, DAPD, dOTC; nucleotide RTIs, such as, for example, PMEA, PMPA; NNRTIs, such as, for example, nevirapine, delavirdine, efavirenz, 8 and 9-Cl TIBO (tivirapine), loviride, TMC-125, TMC-120, MKC442, UC 781, Capravirine, DPC 961, DPC963, DPCO82, DPC083; calanolide A, SJ-3366, TSAO, 4"-deaminated TSAO; RNAse H inhibitors, such as, for example, SP1093V, PD126338; TAT inhibitors, such as, for example, RO-5-3335, K12, K37; integrase inhibitors, such as, for example, L 708906, L 731988; protease inhibitors, such as, for example, amprenavir, ritonavir, nelfinavir, saquinavir, indinavir, lopinavir, BMS 232632, DPC 681, DPC 684, tipranavir, AG1776, DMP 450, L 756425, PD 178390; glycosylation inhibitors, such as, for example, castanospernine, deoxynojirimycine.

The combination may provide a synergistic effect, whereby viral infectivity and its associated symptoms may be prevented, substantially reduced, or eliminated completely. The compounds of the present invention may also be administered in combination with immunomodulators (e.g., bropirimine, anti-human alpha interferon antibody, IL-2, methionine enkephalin, interferon alpha, and naltrexone) or with antibiotics (e.g., pentamidine isothiorate) to ameliorate, combat, or eliminate HIV infection and its symptoms.

For an oral administration form, the compounds of the present invention or a salt thereof is mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof Polyethylene glycols and polypropylene glycols are also useful as further auxiliaries for other administration forms.

For subcutaneous or intravenous administration, the active compounds, if desired with the substances customary therefor such as solubilizers, emulsifiers or further auxiliaries, are brought into solution, suspension, or emulsion. The compounds of formula (I) and their physiologically tolerable salts can also be lyophilized and the lyophilizates obtained used, for example, for the production of injection or infusion preparations. Suitable solvents are, for example, water, physiological saline solution or alcohols, e.g. ethanol, propanol, glycerol, in addition also sugar solutions such as glucose or mannitol solutions, or alternatively mixtures of the various solvents mentioned.

Suitable pharmaceutical formulations for administration in the form of aerosols or sprays are, for example, solutions, suspensions or emulsions of the compounds of formula (I) or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant. Such a preparation customarily contains the active compound in a concentration from approximately 0.1 to 50%, in particular from approximately 0.3 to 3% by weight.

In order to enhance the solubility and/or the stability of the compounds of formula (I) in pharmaceutical compositions, it can be advantageous to employ $\alpha$-, $\beta$- or $\gamma$-cyclo-dextrins or their derivatives. Also co-solvents such as alcohols may improve the solubility and/or the stability of the compounds of formula (I) in pharmaceutical compositions. In the preparation of aqueous compositions, addition salts of the subject compounds are obviously more suitable due to their increased water solubility.

Appropriate cyclodextrins are $\alpha$-, $\beta$- or $\gamma$-cyclodextrins (CDs) or ethers and mixed ethers thereof wherein one or more of the hydroxy groups of the anhydroglucose units of the cyclodextrin are substituted with $C_{1-6}$alkyl, particularly methyl, ethyl or isopropyl, e.g. randomly methylated $\beta$-CD; hydroxy$C_{1-6}$alkyl, particularly hydroxy-ethyl, hydroxypropyl or hydroxybutyl; carboxy$C_{1-6}$alkyl, particularly carboxymethyl or carboxyethyl; $C_{1-6}$alkylcarbonyl, particularly acetyl; $C_{1-6}$allyloxycarbonyl$C_{1-6}$alkyl or cabboxy$C_{1-6}$alkyloxy$C_{1-6}$alkyl, particularly carboxymethoxypropyl or carboxyethoxypropyl; $C_{1-6}$aLkylcarbonyloxy$C_{1-6}$alkyl, particularly 2-acetyloxypropyl. Especially noteworthy as complexants and/or solubilizers are $\beta$-CD, randomly methylated $\beta$-CD, 2,6-dimethyl-$\beta$-CD, 2-hydroxyethyl-$\beta$-CD, 2-hydroxyethyl-$\gamma$-CD, 2-hydroxypropyl-$\gamma$-CD and (2-carboxymethoxy)propyl-$\beta$-CD, and in particular 2-hydroxypropyl-$\beta$-CD (2-HP-$\beta$-CD).

The term mixed ether denotes cyclodextrin derivatives wherein at least two cyclodextrin hydroxy groups are etherified with different groups such as, for example, hydroxypropyl and hydroxyethyl.

An interesting way of formulating the present compounds in combination with a cyclodextrin or a derivative thereof has been described in EP-A-721,331. Although the formulations described therein are with antifungal active ingredients, they are equally interesting for formulating the present antiretroviral compounds. The formulations described therein are particularly suitable for oral administration and comprise an antifungal as active ingredient, a sufficient amount of a cyclodextrin or a derivative thereof as a solubilizer, an aqueous acidic medium as bulk liquid carrier and an alcoholic co-solvent that greatly simplifies the preparation of the composition. Said formulations may also be rendered more palatable by adding pharmaceutically acceptable sweeteners and/or flavours.

Other convenient ways to enhance the solubility of the compounds of the present invention in pharmaceutical compositions are described in WO-94/05263, PCT application No. PCT/EP98/01773, EP-A-499,299 and WO 97/44014, all incorporated herein by reference.

More in particular, the present compounds may be formulated in a pharmaceutical composition comprising a therapeutically effective amount of particles consisting of a solid dispersion comprising (a) a compound of formula (I), and (b) one or more pharmaceutically acceptable water-soluble polymers.

The term "a solid dispersion" defines a system in a solid state (as opposed to a liquid or gaseous state) comprising at least two components, wherein one component is dispersed more or less evenly throughout the other component or components. When said dispersion of the components is such that the system is chemically and physically uniform or homogenous throughout or consists of one phase as defined in thermo-dynamics, such a solid dispersion is referred to as "a solid solution". Solid solutions are preferred physical systems because the components therein are usually readily bioavailable to the organisms to which they are administered.

The term "a solid dispersion" also comprises dispersions which are less homogenous throughout than solid solutions. Such dispersions are not chemically and physically uniform throughout or comprise more than one phase.

The water-soluble polymer in the particles is conveniently a polymer that has an apparent viscosity of 1 to 100 mPa.s when dissolved in a 2% aqueous solution at 20° C. solution.

Preferred water-soluble polymers are hydroxypropyl methylcelluloses or HPMC. HPMC having a methoxy degree of substitution from about 0.8 to about 2.5 and a hydroxypropyl molar substitution from about 0.05 to about 3.0 are generally water soluble. Methoxy degree of substitution refers to the average number of methyl ether groups present per anhydroglucose unit of the cellulose molecule. Hydroxy-propyl molar substitution refers to the average number of moles of propylene oxide which have reacted with each anhydroglucose unit of the cellulose molecule.

The particles as defined hereinabove can be prepared by first preparing a solid dispersion of the components, and then optionally grinding or milling that dispersion. Various techniques exist for preparing solid dispersions including melt-extrusion, spray-drying and solution-evaporation, melt-extrusion being preferred.

It may further be convenient to formulate the present antiretrovirals in the form of nanoparticles which have a surface modifier adsorbed on the surface thereof in an amount sufficient to maintain an effective average particle size of less than 1000 nm. Useful surface modifiers are believed to include those which physically adhere to the surface of the antiretroviral agent but do not chemically bond to the antiretroviral agent.

Suitable surface modifiers can preferably be selected from known organic and inorganic pharmaceutical excipients. Such excipients include various polymers, low molecular vweight oligomers, natural products and surfactants. Preferred surface modifiers include nonionic and anionic surfactants.

Yet another interesting way of formulating the present compounds involves a pharmaceutical composition whereby the present antiretrovirals are incorporated in hydrophilic polymers and applying this mixture as a coat film over many small beads, thus yielding a composition with good bioavailability which can conveniently be manufactured and which is suitable for preparing pharmaceutical dosage forms for oral administration.

Said beads comprise (a) a central, rounded or spherical core, (b) a coating film of a hydrophilic polymer and an antiretroviral agent and (c) a seal-coating polymer layer.

Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

The dose of the present compounds or of the physiologically tolerable salt(s) thereof to be administered depends on the individual case and, as customary, is to be adapted to the conditions of the individual case for an optimum effect. Thus it depends, of course, on the frequency of administration and on the potency and duration of action of the compounds employed in each case for therapy or prophylaxis, but also on the nature and severity of the infection and symptoms, and on the sex, age, weight and individual responsiveness of the human or animal to be treated and on whether the therapy is acute or prophylactic. Customarily, the daily dose of a compound of formula (I) in the case of administration to a patient approximately 75 kg in weight is 1 mg to 1 g, preferably 3 mg to 0.5 g. The dose can be administered in the form of an individual dose, or divided into several, e.g. two, three, or four, individual doses.

Organic Synthesis of Hexahydrofuro[2,3-b]furan-3-yl-N-{3-[(1,3-Benzodioxol-5-ylsufonyl)(isobutyl)amino]-1-benzyl-2-hydroxypropyl}carbamate The synthesis of hexahydrofuro[2,3-b]furan-3-yl-N- {3-[(1,3-benzodioxol-5-ylsufonyl) (isobutyl)amino]-1-benzyl-2-hydroxypropyl}carbamate was accomplished via a coupling step between the bis-tetrahydrofuran ring and the corresponding benzodioxolyl amine as outlined below.

1)Synthesis of Hexahydrofuro[2.3-b]furan-3-ol 5

The racemic synthesis of bis-tetahydrofuran (bis-THF) 5 was accomplished as illustrated in Scheme 1, according to the procedure of Ghosh et al., *J. Med Chem.* 39:3278–3290 (1996). Reaction of commercial 2,3 dihydrofuran with N-iodosuccinimide and propargyl alcohol in methylene chloride at 0–25° C. or 2 hours gave the iodo ether 2 (yield 88%). Radical cyclization of the iodo ether 2 with tributyltin hydride in toluene at 80° C. in the presence of a catalytic amount of 2,2'-azobisisobutyronitrile (AIBN) afforded the bicyclic acetal 3. Ozonolytic cleavage produced ketone 4. Reduction of the resulting ketone with sodium borohydride in ethanol at −15° C. furnished the racemic endo alcohol 5 (see Scheme 1).

Scheme 1

2) Synthesis of the Amino Alcohol 8 N-{3-[(1,3-Benzodioxol-5-ylsufonyl) (isobutyl)amino]-1-benzyl-2-hydroxypropyl}amine Reduction of acyl chloride 9 with NaBH$_4$ in 1:1 methanol:tetrahydrofiuran (step a, Scheme 2 below) produced the racemates 10a and 10b, which were separated and the appropriate enantiomer reacted with KOH in ethanol (step b,c) to produce the epoxide 11 according to published procedures (Getinan, et al., *J. Med Chem.* 36:288–291 (1993), Luly et al.,*J. Org. Chem.* 52(8):1487–1492 (1987)). The epoxide was treated with an excess of isoamylamine in refluxing 2-propanol (step d) to generate the amino alcohol 12. The amino alcohol 12 was then reacted with 1,3-benzodioxol-5-ylsulfonyl-chloride (step e) which generated amino alcohol 8 with a carbobenzoxy (Cbz) protected amine. Hydrogenation of the Cbz group with 10% Pd/C and H$_2$ in methanaol (step f) provided the free amino alcohol 8. These steps were accomplished according to generally published procedures (Vazquez et al., *J. Med Chem.* 38:581–584 (1995), Scheme 2).

Scheme 2

3) Synthesis of Hexahydrofuro[2,3-b]furan-3-yl-N-{3-[1,3-benzodioxol-5-ylsufonyl)(isobutyl)amino]-1-benzyl-2-hydroxypropyl}carbamate Reaction of the bis-tetrahydrofuran ligand 5 with disuccinimidyl carbonate 6 and triethylamine in methylene chloride afforded the carbonate 7 which was mixed in situ with amine 8. This coupling produced the final compound 13 (Scheme 3). Compound 13 is a mixture of 2 diastereoisomers having the stereoisomeric forms as defined for compounds 1 and w in the table A. This mixture can be separated using art-known separation techniques.

Alternatively, the pure enantiomeric form corresponding to compound 1 and w, hereinafter referred to as compounds 14 and 15 can be prepared by resolving the racermic bis-THF 5 via an enzymatic resolution step as described in Tetrahedron Letters, 36, 4, (1995), 505–508, incorporated herein by reference. The enantiomeric pure bis-THF intermedites can then be reacted analogously to the procedure described above, thus obtaining enantiomerically pure compound 14 and 15.

Scheme 3

Experimental Section

To a stirred solution of (500 mg, 3.84 mmol) of (3R,3aS, 6aR)-3-hydroxyhexa-hydrofuro[2,3-b]-furan 5 (Scheme 1) in $CH_2Cl_2$ (50 ml) at 25° C., disuccinimidyl carbonate 6 (1.08 g, 4.23 mmol) and triethylamine (0.77 g, 7.68 mmol) were added. The resulting mixture was stirred for 6 h at 25° C. and the amine 8 (Scheme 2, 2.42 g, 5.76 mmol) was added. The resulting solution was washed with water and dried over anhydrous $Na_2SO_4$. Evaporation of solvent under reduced pressure afforded a residue which was purified by chromatography ($CH_2Cl_2$/MeOH: 98/2) which famished 1.36 g (62%) of the inhibitor 13 (Scheme 3) of the instant invention as a white solid.

The $^1$H-NMR spectrum in $CDCl_3$ of compound 13 was as follows: 7.4–7.1 (br m, 7H). 6.9 (d, J=8.1 Hz, 1H), 6.1 (s, 2H), 5.7 (d, J=5.1 Hz, 1H), 5 (d, J=6.7Hz, 1H), 5,1–4.8 (br m, 1H), 4–3.4 (br m, 7H), 3.25–2.6 (br m, 6H), 2.35–1.2 (br m, 4H), 1.17–0.7 (br me 6H). Likewise, the $^{13}$C-NMR spectrum in $CDCl_3$ was as follows: 151 (CO), 148–138 (C—O), 132–129.4–129.34–128.55–126.67–126.59–123.1 (Ar—C), 109.16–108.36–107.52–102.36 (CH—O), 73.43–72.58–70.73–69.47–58.87–53.78–45.04–36–35–27, 27–25.76–20.1–19.85. Mass spectrometry gave the expected ion (m/z) 577, corresponding to $M^++H$.

The resulting compound 13 and compound 14 were then tested for biological and antiviral activity in several assays as described below. Surprisingly, these compounds were found to be more effective and more active as a protease inhibitor than previously known compounds.

Antiviral Analyses

Compound 13 and compound 14 were then examined for anti-viral activity in a cellular assay. The assay demonstrated that these compounds exhibited potent anti-HIV activity against a wild type laboratory HIV strain. The cellular assay was performed according to the following procedure.

Cellular Assay Experimental Method

HIV- or mock-infected MT4 cells were incubated for five days in the presence of various concentrations of the inhibitor. At the end of the incubation period, all HIV-infected cells have been killed by the replicating virus in the control cultures in the absence of any inhibitor. Cell viability is measured by measuring the concentration of MTT, a yellow, water soluble tetrazolium dye that is converted to a purple, water insoluble formazan in the mitochondria of living cells only. Upon solubilization of the resulting formazan crystals with isopropanol, the absorbance of the solution is monitored at 540 nm. The values correlate directly to the number of living cells remaining in the culture at the completion of the five day incubation. The inhibitory activity of the compound was monitored on the virus-infected cells and was expressed as $IC_{50}$ and $IC_{90}$. These values represent the amount of the compound required to protect 50% and 90%, respectively, of the cells from the cytopathogenic effect of the virus. The toxicity of the compound was measured on the mock-infected cells and was expressed as $CC_{50}$, which represents the concentration of compound required to inhibit the growth of the cells by 50%. The selectivity index (SI) (ratio $CC_{50}/IC_{50}$) is an indication of the selectivity of the anti-HIV activity of the inhibitor.

Cellular Assay Results

Compound 13 exhibits an $IC_{50}$ of 1.1 nM and an $IC_{90}$ of 2.4nM (representing the median value of 12 determinations)

against HIV-1 strain LAI. The $CC_{50}$ of compound 13 is 15.3 μM and its SI is 13,900. Compound 14 exhibits an $IC_{50}$ of 0.8 nM against HIV-1 strain LAI. The $CC_{50}$ of compound 13 is greater than 100 μM.

Protein Binding Analyses

Human serum proteins like albumin (HSA) or alpha-1 acid glycoprotein (AAG) are known to bind many drugs, resulting in a possible decrease in the effectiveness of those compounds. In order to determine whether compound 13 would be adversely effected by this binding, the anti-HIV activity of the compound was measured in the presence of physiological concentrations of HSA or AAG, thus evaluating the effect of the binding of the inhibitor to those proteins.

Results

In a typical experiment, HSA at a concentration of 45 mg/ml had no effect on the potency of compound 13. AAG at a concentration of 2 mg/ml decreased the potency of compound 13 by two to four fold.

Antiviral Spectrum

Because of the increasing emergence of drug resistant HIV strains, compound 13 and compound 14 were tested for its potency against HIV strains harbouring several mutations. These mutations are associated with resistance to protease inhibitors and result in viruses that show various degrees of phenotypic cross-resistance to five of the currently commercially available drugs (Saquinavir, Ritonavir, Nelfinavir, Indinavir and Amprenavir).

Results

Figure 2:
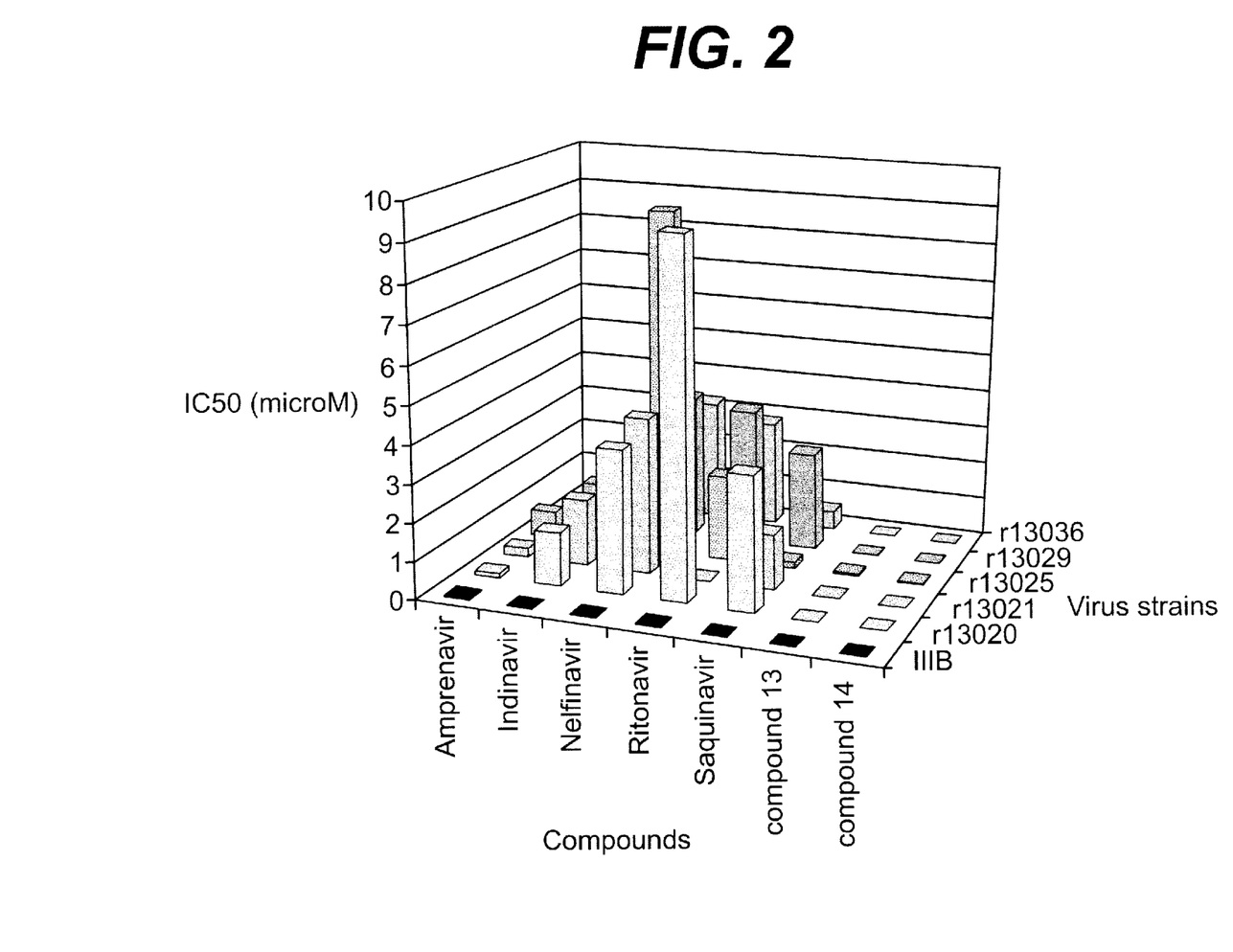
FIG. 2 compares the activity of the inventive compounds 13 and 14 and several commercially available anti-viral compounds against a small panel of viral strains.

Table 1 shows the results of this testing as $IC_{50}$ values in μM. Compounds 13 and 14 are effective in inhibiting even these resistant viruses at low concentrations that are well below attainable plasma levels. FIG. 2 shows a comparison of the fold resistance of various viral strains to commercially available protease inhibitors and compound 13. The strains surprisingly show an enhanced sensitivity to the compound 13 as compared to Saquinavir (SAQ), Ritonavir (RIT), Indinavir (IND), Nelfinavir (NEL), and Amprenavir (AMP).

TABLE 1

Activity of compounds 13 and 14, and 5 commercial protease inhibitors against Protease Inhibitor Resistant HIV Strains

| Strain | Resistance associated mutations | SAQ | RIT | ND | NEL | AMP | Comp 14 | Comp 13 |
|---|---|---|---|---|---|---|---|---|
| LAI | | 0.0079 | 0.0304 | 0.0276 | 0.0331 | 0.0359 | 0.0008 | 0.0014 |
| r13020 | L10I, K20R, M36I, I54V, A71V, V82T, I84V | 3.51 | 9.28 | 1.38 | 3.75 | 0.107 | 0.0008 | 0.0014 |
| r13021 | L10I, K20R, L24I, M36I, I54V, L63P, A71V, V82T, I84V | 1.45 | >10 | 1.75 | 4.10 | 0.212 | 0.0015 | 0.0055 |
| r13022 | K20R, M36I, M46I/M, I54V, L63P, A71 V/I, V82T, L90M | 0.665 | >10 | 1.70 | 4.03 | 0.181 | 0.0011 | 0.0017 |
| r13023 | L10I, M36I/M, I54V/I, L63P, A71V, G73S, I84V, L90M | 0.783 | 3.82 | 0.680 | 1.02 | 0.217 | 0.0028 | 0.0068 |
| r13024 | L10I, M36I, L63P, A71V, G73S, I84V, L90M | 2.09 | 2.85 | 1.07 | 3.26 | 0.180 | 0.0055 | 0.0081 |
| r13025 | L10I, M46I, L63P, A71V, I84V | 0.157 | 2.24 | 1.25 | 9.13 | 0.661 | 0.0328 | 0.0454 |
| r13026 | L10I, M46I, I54V, L63P, A71V, V82T, I84V | 1.99 | >10 | 2.72 | 1.22 | 0.136 | 0.0008 | 0.0014 |
| r13027 | L10M/I, K20R, M36I, L63P, A71V, G73S, V77I, I84V, L90M | 2.92 | 3.14 | 0.714 | 3.20 | 0.645 | 0.0073 | 0.0074 |
| r13029 | L10I/L, M36I, M46L, L63P, A71V, I84V, N88D, L90M | 2.61 | 3.60 | 0.922 | 3.79 | 0.214 | 0.0052 | 0.0070 |
| r13030 | L10V/I, M36I, I54V, L63P, A71V, V82T, L90M | 0.173 | 2.99 | 0.574 | 0.995 | 0.0491 | 0.0002 | 0.0004 |
| r13031 | G48V, I54V, V77I, V82A, L90M/L | 0.673 | 0.856 | 0.1542 | 0.497 | 0.0341 | 0.0003 | 0.0005 |
| r13033 | L10I, M46L, I54V, L63P, A71V, V82A, L90M | 0.0521 | 3.47 | 0.848 | 1.19 | 0.194 | 0.0011 | 0.0017 |
| r13034 | L10I, M36I, I54V, L63P A71V, I84V | 1.01 | >10 | 0.638 | 1.99 | 0.677 | 0.0055 | 0.0080 |
| r13035 | D30N, L63P, V77I, N88D | 0.0053 | 0.0311 | 0.0074 | 0.361 | 0.0105 | 0.0002 | 0.0003 |

TABLE 1-continued

Activity of compounds 13 and 14, and 5 commercial protease inhibitors against Protease Inhibitor Resistant HIV Strains

| Strain | Resistance associated mutations | SAQ | RIT | ND | NEL | AMP | Comp 14 | Comp 13 |
|---|---|---|---|---|---|---|---|---|
| r13036 | L10I, L63P, A71V, G73S, L90M | 0.514 | 2.83 | 0.638 | 3.25 | 0.445 | 0.0029 | 0.0054 |
| r13037 | L10I, M46I, I54V, L63P, A71T, V77I, V82A, L90M | 0.0274 | 2.72 | 0.196 | 0.656 | 0.165 | 0.0005 | 0.0003 |

Bioavailability

The oral absorption of compound 13 was then measured in rats to determine bioavailability. The compound was administered by gavage to rats, as a single dose of 20 mg/kg in PEG400. Animals were sacrificed at different time points after administration, whole blood was collected and serum prepared by standard methods. Concentration of the compound in serum was determined by titrating the anti-HIV activity present in the sample according to the procedure described above.

Bioavailability Results

Figure 1:
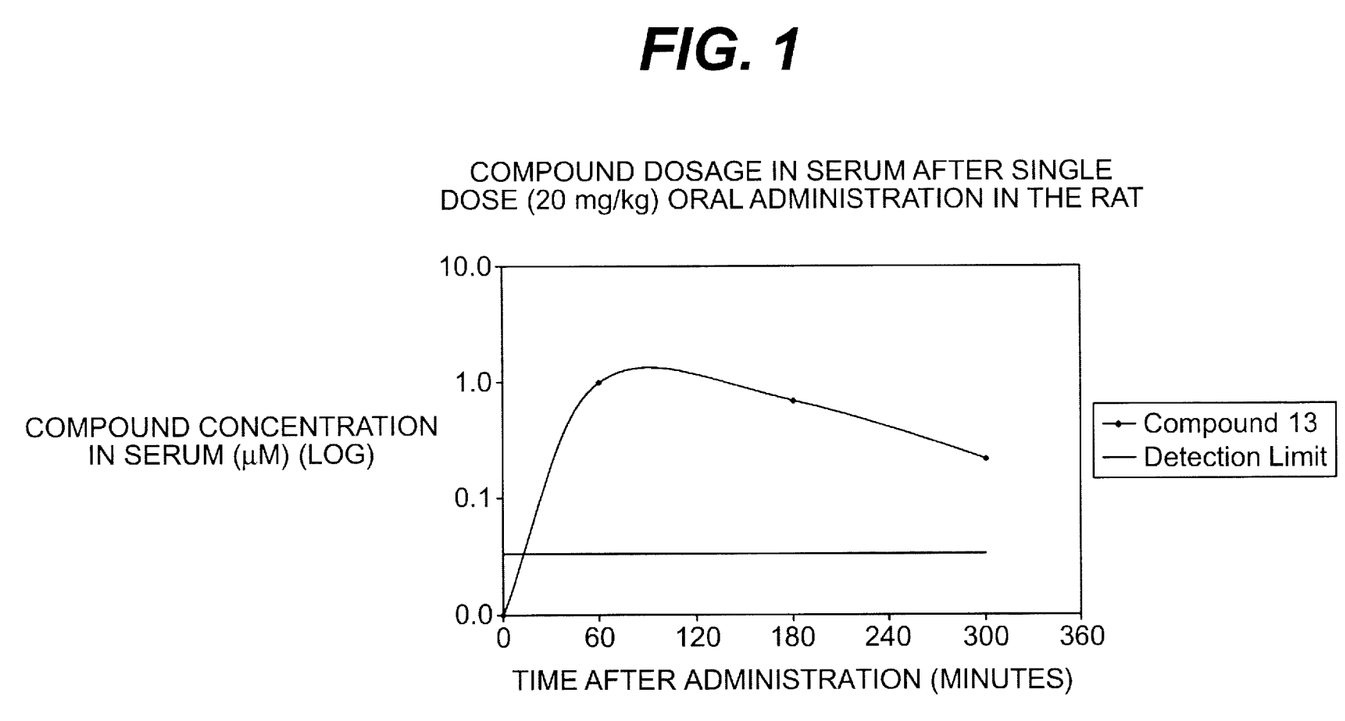
FIG. 1 illustrates the serum concentration of the compound 13 after a single oral dose administration as a function of time.

The results are shown in Table 2 and illustrated graphically in FIG. 1. Compound 13 serum concentration rises to 1 $\mu$M 1 hour after oral administration and is still superior to the $IC_{50}$ of the compound against protease inhibitors multi-resistant strains up to 3 hours after administration. Compound 13 therefore has a significant advantage in terms of therapeutic margin. This unexpectedly high plasma bioavailability is especially important against resistant viruses.

TABLE 2

Compound Concentration in Serum after Oral Administration

| Time after administration (minutes) | Compound concentration in serum ($\mu$M) compound 13 |
|---|---|
| 0 | 0.0000 |
| 60 | 0.9858 |
| 180 | 0.6869 |
| 300 | 0.2159 |

The present invention may be embodied in other specific forms without departing from its spirit or essential characteristics. The described embodiments are to be considered in all respects as illustrative only and not restrictive. The scope of the present invention is, therefore, indicated by the appended claims rather than by the foregoing description. All changes which come within the meaning and range of equivalency of the claims are to be embraced within their scope.

We claim:
1. A compound having the formula

(I)

or an N-oxide, salt, ester, prodrug or metabolite thereof, in any stereoisomeric form, or a mixture of such compounds.

2. A compound as claimed in claim 1 in an enantiomerically pure form.

3. A compound according to claim 1 wherein the compound is or an N-oxide, salt, ester, prodrug or metabolite thereof.

4. A compound as claimed in claim 1, which is a pharmaceutically tolerable salt form of the compound having the formula (I).

5. A compound as claimed in claim 1, which is a prodrug form of the compound having the formula (I).

6. A pharmaceutical composition, comprising an effective amount of at least one compound as claimed in claim 1 and a pharmaceutically tolerable excipient.

7. A method of inhibiting a protease of a retrovirus in a mammal infected with said retrovirus, comprising administering a protease inhibiting amount of at least one compound according to claim 1 to said mammal in need thereof.

8. A method of treating or combating infection or disease associated with retrovirus infection in a mammal, comprising administering an effective amount of at least one compound according to claim 1 to said mammal.

9. The method as claimed in claim 7, wherein said mammal is a human.

10. A method of inhibiting retroviral replication, comprising contacting a retrovirus with an effective amount of at least one compound according to claim 1.

11. The method as claimed in claim 7 wherein the retrovirus is a human immunodeficiency virus (HIV).

12. A compound as claimed in any one of claims 1 to 5 for use as a medicine.

13. The method as claimed in claim 8, wherein said mammals a human.

14. The method as claimed in claim 8, wherein the retrovirus is a human immunodeficiency virus (HIV).

15. The method as claimed in claim 10, wherein the retrovirus is a human immunodeficiency virus (HIV).

16. The method as claimed in claim 14, wherein the HIV virus is a multi-drug resistant strain.

17. The method as claimed in claim 15, wherein the HIV virus is a multi-drug resistant strain.

* * * * *

UNITED STATES PATENT AND TRADEMARK OFFICE
CERTIFICATE OF CORRECTION

| | | |
|---|---|---|
| PATENT NO. | : 6,649,651 B1 | |
| APPLICATION NO. | : 10/089991 | |
| DATED | : November 18, 2003 | |
| INVENTOR(S) | : Piet T. B. P. Wigernick et al. | |

It is certified that error appears in the above-identified patent and that said Letters Patent is hereby corrected as shown below:

Column 1, line 14:
    Insert the following new Paragraph after the first paragraph directed to the cross- reference to related applications:

--STATEMENT OF FEDERALLY SPONSORED RESEARCH

The U.S. Government may have certain rights in the invention described herein. --.

Signed and Sealed this

Second Day of January, 2007

JON W. DUDAS
*Director of the United States Patent and Trademark Office*